(12) United States Patent
Hill

(10) Patent No.: US 6,871,096 B2
(45) Date of Patent: Mar. 22, 2005

(54) SYSTEM AND METHOD FOR BI-VENTRICULAR FUSION PACING

(75) Inventor: Michael R. S. Hill, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 471 days.

(21) Appl. No.: 10/000,474

(22) Filed: Oct. 26, 2001

(65) Prior Publication Data

US 2003/0083700 A1 May 1, 2003

(51) Int. Cl.$^7$ .............................................. A61N 1/365
(52) U.S. Cl. ...................................................... 607/25
(58) Field of Search ............................. 607/25, 4, 5, 9, 607/14, 15, 26, 123

(56) References Cited

U.S. PATENT DOCUMENTS

| | | | |
|---|---|---|---|
| 3,937,226 A | 2/1976 | Funke | 128/419 |
| 4,088,140 A | 5/1978 | Rockland et al. | 128/419 |
| 4,332,259 A | 6/1982 | McCorkle, Jr. | 128/786 |
| 4,354,497 A | 10/1982 | Kahn | 128/419 |
| 4,428,378 A | 1/1984 | Anderson et al. | 128/419 |
| 4,458,677 A | 7/1984 | McCorkle, Jr. | 128/786 |
| 4,548,203 A | 10/1985 | Tacker, Jr. et al. | 128/419 |

(List continued on next page.)

OTHER PUBLICATIONS

Auricchio et al., Effect of Pacing Chamber and Atrioventricular Delay on Acute Systolic Function of Paced Patients With Congestive Heart Failure, *Circulation*, vol. 23, p. 2993–3001, Jun. 15, 1999.

(List continued on next page.)

*Primary Examiner*—Jeffrey R. Jastrzab
(74) *Attorney, Agent, or Firm*—Girma Wolde-Michael; Paul H. McDowall

(57) ABSTRACT

Bi-ventricular cardiac pacing systems and systems for improving cardiac function for heart failure patients that pace and sense in right and left ventricles of the heart and particularly pace in one of the right and left ventricles after an AV delay timed from a preceding atrial event and after a spontaneous depolarization in the other of the right and left ventricles to achieve fusion pacing. An A-RVp delay and an A-LVp delay are each determined from an intrinsic sensed A-RVs delay and an intrinsic A-LVs delay. If the derived A-LVp delay becomes substantially equal to or shorter than the intrinsic A-RVs delay, then the A-RVp delay is decremented to be shorter than the A-LVp delay. Bi-ventricular pacing of the RV and LV is then established closely timed to the intrinsic RV and LV depolarizations.

27 Claims, 7 Drawing Sheets

U.S. PATENT DOCUMENTS

| | | |
|---|---|---|
| 4,928,688 A | 5/1990 | Mower .................... 128/419 |
| 5,052,388 A | 10/1991 | Sivula et al. ............ 128/419 |
| 5,144,949 A | 9/1992 | Olson ..................... 128/419 |
| 5,174,289 A | 12/1992 | Cohen ..................... 128/419 |
| 5,267,560 A | 12/1993 | Cohen ....................... 607/25 |
| 5,340,361 A | 8/1994 | Sholder ..................... 607/24 |
| 5,403,356 A | 4/1995 | Hill et al. ................. 607/14 |
| 5,514,161 A | 5/1996 | Limousin ..................... 607/9 |
| 5,534,506 A | 7/1996 | Morgan et al. ............ 514/185 |
| 5,584,867 A | 12/1996 | Limousin et al. ............. 607/9 |
| 5,626,620 A | 5/1997 | Kieval et al. ................ 607/9 |
| 5,626,623 A | 5/1997 | Kieval et al. ............... 607/23 |
| 5,674,259 A | 10/1997 | Gray ......................... 607/20 |
| 5,716,383 A | 2/1998 | Kieval et al. ................ 607/9 |
| 5,720,768 A | 2/1998 | Verboven-Nelissen ........ 607/9 |
| 5,749,906 A | 5/1998 | Kieval et al. ................ 607/9 |
| 5,792,203 A | 8/1998 | Schroeppel ................. 607/30 |
| 5,797,970 A | 8/1998 | Pouvreau ..................... 607/9 |
| 5,902,324 A | 5/1999 | Thompson et al. ............. 607/9 |
| 6,129,744 A | 10/2000 | Boute ........................ 607/25 |
| 6,144,880 A | 11/2000 | Ding et al. |
| 2001/0012953 A1 | 8/2001 | Molin et al. |

OTHER PUBLICATIONS

Daubert et al., "Permanent Left Ventricular Pacing with Transvenous Leads Inserted Into the Coronary Veins, " *PACE*, vol. 21, p 239–245, Jan. 1998, Part II.

Daubert et al., "Permanent Dual Atrium Pacing in Major Interatrial Conduction Blocks: A Four Year Experience," *PACE*, vol. 16, p 885, Apr. 1993, Part II.

Durrer et al., "Total Excitation of the Isolated Human Heart," *Circulation*, vol. XLI, p 899–912, Jun. 1970.

McDonald et al., "Permanent Pacing as Treatment for Hypertrophic Cardiomyopathy," *American Journal of Cardiology*, vol. 68, p 108–110, Jul. 1991.

SYSTEM AND METHOD FOR BI-VENTRICULAR FUSION PACING

FIELD OF THE INVENTION

The present invention pertains to bi-ventricular cardiac pacing systems for improving cardiac function for heart failure patients that pace and sense in right and left ventricles of the heart and particularly pace in one of the right and left ventricles after an AV delay timed from a preceding atrial sense or atrial pace pulse characterized as an A-RVp delay and an A-LVp delay that are each determined from the intrinsic sensed A-RVs delay or the A-LVs delay to effect a fusion of delivered left ventricular pacing pulses with intrinsic depolarizations of the right ventricle.

BACKGROUND OF THE INVENTION

Dual chamber pacing systems operating in the multi-programmable, VDD, DDD and DDDR pacing modes have been widely adopted in implantable dual chamber pacemakers and certain implantable cardioverter/defibrillators (ICDs) for providing atrial and ventricular synchronized pacing on demand. A DDD pacemaker implantable pulse generator (IPG) includes an atrial sense amplifier to detect atrial depolarizations or P-waves in the right atrium (RA) and generate an atrial sense event (A-EVENT) signal, a ventricular sense amplifier to detect ventricular depolarizations or R-waves in the right ventricle (RV) and generate a ventricular sense event (V-EVENT) signal, atrial and ventricular pacing pulse generators providing atrial and ventricular pacing (A-PACE and V-PACE) pulses, respectively, and an operating system governing pacing and sensing functions. If the atria fail to spontaneously beat within a pre-defined time interval (atrial escape interval), the pacemaker supplies an A-PACE pulse to the RA through an appropriate lead system. The IPG supplies a V-PACE pulse to the RV through an appropriate lead system at the time-out of an AV delay timed from a preceding A-EVENT or generation of an A-PACE pulse unless a non-refractory V-EVENT is generated in response to an R-wave during the AV delay. Such AV synchronous DDD pacemakers have the capability of tracking the patient's natural sinus rhythm and preserving the hemodynamic contribution of the atrial contraction over a wide range of heart rates.

AAV synchronous DDD pacemaker can operate in or be programmed to operate in the VDD mode when the atria function in a normal sinus rhythm between a programmed lower rate limit (LRL) and a programmmed upper rate limit (URL). Thus, the atria are not paced in the VDD pacing mode.

The rate-adaptive DDDR and VDDR pacing mode functions in the above-described manner but additionally provides rate modulation of a pacing escape interval between the programmable LRL and URL as a function of a physiologic signal or rate control parameter (RCP) developed by one or more physiologic sensors and related to the need for cardiac output. Reliance on the intrinsic atrial heart rate is preferred if it is appropriately between the URL and the programmed lower rate. At times when the intrinsic atrial rate is inappropriately high, a variety of "mode switching" schemes for effecting switching between tracking modes and non-tracking modes (and a variety of transitional modes) based on the relationship between the atrial rate and the sensor derived pacing rate have been proposed as exemplified by commonly assigned U.S. Pat. No. 5,144,949, incorporated herein by reference in its entirety.

The VDD, DDD and DDDR pacing modes were initially perceived to be of greatest benefit to cardiac patients whose hearts have an intact sinoatrial (SA) node that generates the atrial depolarizations detectable as P-waves, but also suffer defective A-V conduction, or AV block, wherein the ventricles fail to depolarize in synchrony with the atria. The RV is paced in the DDD pacing mode in synchrony with the atria after a timed out AV delay and is generally adequate to restore cardiac output for sedentary patients. Active patients with Sick Sinus Syndrome (SSS) have an intrinsic atrial rate that can be sometimes appropriate, sometimes too fast, and sometimes too slow. For SSS patients, the DDDR pacing mode provides some relief by pacing the atria and ventricles at a physiologic rate determined by an algorithm responsive to the RCP indicative of the patient's metabolic needs.

A loss of A-V electrical and mechanical synchrony can result in series of asynchronous atrial and ventricular depolarizations at independent rates that periodically result in an atrial depolarization that closely follows a ventricular depolarization. When this occurs, the left atrium (LA) contracts against a closed mitral valve, resulting in impeded venous return from the pulmonary vasculature due to increased atrial pressure and possibly even retrograde blood flow into the pulmonary venous circulation. As a result, the volume and pressure in the pulmonary venous circulation rise. Increased pulmonary pressures may lead to pulmonary congestion and dyspnea. Distension of the pulmonary vasculature may be associated with peripheral vasodilation and hypotension. In addition, the concomitant atrial distension is associated with increased production of atrial natriuretic factor and increases the susceptibility to atrial arrhythmias and possibly rupture of the atrial wall. Finally, turbulence and stagnation of blood within the atrium increase the risk of thrombus formation and subsequent arterial embolization. Maintenance of AV mechanical synchrony is therefore of great importance as set forth in greater detail in commonly assigned U.S. Pat. No. 5,626,623, incorporated herein by reference in its entirety.

Although DDD and DDDR pacing systems were initially offered to treat patients hearts exhibiting A-V conduction defects as described above, the value of dual chamber DDD or DDDR cardiac pacing treatment of patients suffering from HOCM (Hypertrophic Obstructive Cardiomyopathy) has been recognized in the literature. See, for example, "Permanent Pacing As Treatment For Hypertrophic Cardiomyopathy," by Kenneth M. McDonald et al., *American Journal of Cardiology*, Vol. 68, pp. 108–110, Jul. 1991. HOCM is characterized by a narrowed left ventricular outflow tract (LVOT), which causes a significant increase in the left ventricular end systolic pressure. The narrowed LVOT is caused by an increased thickness of the interventricular septum that obstructs blood flow out of the LV during systole, the time of cardiac ejection. Studies have indicated that patients suffering from HOCM may benefit from a specific mode of DDD pacing, wherein a V-PACE is delivered to the RV apex or septal wall in carefully timed AV synchrony with the preceding A-EVENT sensed in the RA or the preceding A-PACE delivered in the RA. Pacing the RV apex before spontaneous atrio-ventricular conduction activates the ventricles is understood to alter the ventricular septal activation pattern. Since the RV is caused to contract first, it pulls the septum toward the RV thereby reducing the LVOT obstruction.

The prior art techniques for AV synchronous pacing of HOCM patients, e.g., those disclosed in U.S. Pat. No. 5,340,361, recognize the necessity to periodically evaluate the pacing AV delay. The patient's intrinsic AV delay generally will change with heart rate, i.e., from rest to exercise. Moreover, simultaneous drug treatment such as beta blockers may also modify the intrinsic AV delay and require renewed evaluation of the AV delay. The importance of periodically making an accurate determination of the optimized pacing AV delay thus takes on significance. If the pacing AV delay is adjusted to a value that is too short, in order to ensure complete ventricular capture, the atrial contribution to ventricular filling may be compromised. However, if the pacing AV delay is adjusted to too great a value, ventricular capture is compromised, and there may be episodes of no ventricular pacing or the ventricular pace may not contribute the best possible reduction of the LVOT obstruction. Accordingly, it is important in this therapy to be able to continuously or periodically adjust the pacing AV delay to optimize it for HOCM therapy. Commonly assigned U.S. Pat. Nos. 5,534,506, 5,626,620, 5,626,623, 5,716,383, and 5,749,906 disclose ways of optimizing the pacing AV delay for pacing hearts exhibiting HOCM.

It has also been proposed that various conduction disturbances involving both bradycardia and tachycardia of a heart chamber could benefit from pacing pulses applied at multiple pace/sense electrode sites positioned in or about a single heart chamber or in the right and left heart chambers in synchrony with a depolarization which has been sensed at least one of the pace/sense electrode sites. It is believed that atrial and left ventricular cardiac output can be significantly improved when left and right chamber synchrony is restored, particularly in patients suffering from dilated cardiomyopathy (DCM) and congestive heart failure (CHF).

CHF is defined generally as the inability of the heart to deliver enough blood, i.e., to supply sufficient cardiac output, to the peripheral tissues to meet metabolic demands. Frequently CHF is manifested by left ventricular dysfunction (LVD), but it can have a variety of sources including HOCM, different conduction defects, cardiomyopathies, etc. The natural electrical activation system through the heart involves sequential events starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and final distribution to the distal myocardial terminals via the Purkinje fiber network as shown in FIG. 1.

FIG. 1 is an illustration of transmission of the cardiac depolarization waves through the RA, LA, RV and LV of heart 10 in a normal electrical activation sequence at a normal heart rate with the conduction times exhibited thereon in seconds. The cardiac cycle commences normally with the generation of the depolarization impulse at the SA Node in the right atrial wall and its transmission through the atrial conduction pathways of Bachmann's Bundle and the Internodal Tracts at the atrial level into the left atrial septum. The RA depolarization wave reaches the AV node and the atrial septum within about 40 msec and reaches the furthest walls of the RA and LA within about 70 msec, and the atria complete their contraction as a result of the electrical activation. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and is then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent the RV or LV exceeds a threshold amplitude, it is detected as a sensed R-wave. Although the location and spacing of the external ECG electrodes or implanted ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier. The typical normal conduction ranges of sequential activation are also described in the article by Durrer et al., entitled "Total Excitation of the Isolated Human Heart", in *CIRCULATION* (Vol. XLI, pp. 899–912, June 1970).

This normal electrical activation sequence becomes highly disrupted in patients suffering from advanced CHF and exhibiting an intra-atrial conduction defect (IACD) and/or an interventricular conduction defect (IVCD). A common type of intra-atrial conduction defect is known as or intra-atrial block (IAB), a condition where the atrial activation is delayed in getting from the RA to the LA. In left bundle branch block (LBBB) and right bundle branch block (RBBB), the activation signals are not conducted in a normal fashion along the right or left bundle branches respectively. Thus, in a patient with bundle branch block, the activation of the RV and the LV is slowed, and the QRS is seen to widen due to the increased time for the activation to traverse the conduction path. These conduction defects exhibit great asynchrony between the RV and the LV due to conduction disorders along the Bundle of His, the Right and Left Bundle Branches or at the more distal Purkinje Terminals. Typical intra-ventricular peak-peak asynchrony can range from 80 to 200 msec or longer. In RBBB and LBBB patients, the QRS complex is widened far beyond the normal range to from >120 msec to 250 msec as measured on surface ECG. This increased QRS width demonstrates the lack of synchrony of the right and left ventricular depolarizations and contractions.

AV synchronized pacing of CHF hearts exhibiting DCM (CHF/DCM hearts) and lack of ventricular synchrony due to an IVCD of BBB condition do not necessarily benefit from the typically long AV delay that is determined to be optimal for HOCM patients. Frequently, CHF/DCM hearts exhibit intrinsic A-V (alternatively referred to as P-Q) conduction intervals or delays between 180 ms–260 ms with LBBB patterns or IVCD, and widened QRS complexes >120 ms, and also exhibit A-V conduction defects, including 1° AV Block (AVB). In time, the 1° AV Block can degenerate to 2° AV Block or 3° AV Block. Widened QRS Complexes (>120 ms), caused either by LBBB, IVCD, or RV paced evoked response, represent a significant delay in LV electrical activation and thus a significant delay in LV mechanical activation.

Optimal AV delay timing is obtained when the onset of LV contraction occurs immediately upon completion of the LA contribution (Left Atrial Kick) in late diastole. At this moment, the LV filling (preload) is maximum, and the Frank-Starling Relationship between LV stretch and LV contraction is the greatest. This will result in maximum LV stroke volume ejection, and thus maximum Cardiac Index/Cardiac Output to be realized. To realize this exact A-V Sequential timing, the AV delay must be fully optimized.

Any delay between the completion of atrial contribution and the start of LV contraction can lead to "Pre-Systolic" mitral regurgitation, resulting in loss of effective LV filling and thus loss of LV stroke volume and reduced cardiac output. In addition, a too long AV delay reduces the diastolic time available for proper LVFT as observed on the diastolic Transmitral Inflow Pattern, resulting in a fusion of the transmitral inflow rapid filling phase (E wave) and active filling phase (A wave) of the Mitral Flow Relationship. A short, optimized AV delay, however, will allow maximum de-fusion of E and A waves, and a maximum LVFT to be realized at any given heart rate, contributing to increased cardiac output.

Thus, cardiac depolarizations that naturally occur in one upper or lower heart chamber are not conducted in a timely fashion either within the heart chamber or to the other upper or lower heart chamber diseased hearts exhibiting LVD and CHF. In such cases, the right and left heart chambers do not contract in optimum synchrony with each other, and cardiac output suffers due to the conduction defects. In addition, spontaneous depolarizations of the LA or LV occur at ectopic foci in these left heart chambers, and the natural activation sequence is grossly disturbed. In such cases, cardiac output deteriorates because the contractions of the right and left heart chambers are not synchronized sufficiently to eject blood therefrom. Hearts evidencing CHF with and without LVD have reduced ejection fraction from the LV thereby reducing stroke volume and promoting pulmonary edema limiting the patient's ability to exercise as described in commonly assigned U.S. Pat. No. 6,129,744. Furthermore, significant conduction disturbances between the RA and LA can result in left atrial flutter or fibrillation.

A number of proposals have been advanced for providing pacing therapies to alleviate heart failure conditions and restore synchronous depolarization and contraction of a single heart chamber or right and left, upper and lower, heart chambers as described in detail in the above referenced '744 patent and in commonly assigned U.S. Pat. Nos. 5,403,356, 5,797,970 and 5,902,324 and in U.S. Pat. Nos. 5,720,768 and 5,792,203. The proposals appearing in U.S. Pat. Nos. 3,937,226, 4,088,140, 4,548,203, 4,458,677, 4,332,259 are summarized in U.S. Pat. Nos. 4,928,688 and 5,674,259. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", *PACE* (Vol. 16, Part II, NASPE Abstract 141, p.885, April 1993); Daubert et al., "Permanent Left Ventricular Pacing With Transvenous Leads Inserted Into The Coronary Veins", *PACE* (Vol. 21, Part II, pp. 239–245, January 1998); Cazeau et al., "Four Chamber Pacing in Dilated Cardiomyopathy", *PACE* (Vol. 17, Part II, pp. 1974–1979, November 1994); and Daubert et al., "Renewal of Permanent Left Atrial Pacing via the Coronary Sinus", *PACE* (Vol. 15, Part II, NASPE Abstract 255, p. 572, April 1992).

Typically, the bi-ventricular pacing systems described in the literature and in patents pace the RV and the LV simultaneously or separated by a programmable V-V pace delay, which is either an RV-LV pace delay or an LV-RV pace delay. Typically, in the prior art, the AV delay is timed out, the first V-PACE is delivered to one of the RV and LV, the V-V pace delay is timed out, and the second V-PACE is delivered to the other of the RV and LV. Or, an A-RV delay and an A-LV delay are started on the atrial pace or atrial sense event, and the RV-PACE and LV-PACE pulses are delivered to the RV and LV, in the predetermined sequence, when they time out. All of these delays are typically made programmable.

In the above-referenced '324 patent, an AV synchronous pacing system is disclosed providing three or four heart chamber pacing through pace/sense electrodes located in or adjacent one or both of the RA and LA and in or adjacent to both the RV and LV. One or two paced AV (PAV) delays defined to follow a selected one or both of the RA-PACE or LA-PACE and sensed AV (SAV) delays are timed from one of the RA-EVENT or the LA-EVENT. A non-refractory RV-EVENT or LV-EVENT detected at the respective RV or LV pace/sense electrodes during the time-out of the prevailing AV delay or V-A escape interval starts a conduction time window (CDW) timer. A LV-PACE or RV-PACE is delivered to the other of the LV or RV pace/sense electrodes at the time-out of the CDW if an LV-EVENT or RV-EVENT is not detected at that site while the CDW times out. The CDW can be set to zero, whereby RV-PACE and LV-PACE pulses are delivered simultaneously to the RV and LV upon time-out of the prevailing AV delay.

Recent findings of studies of such hearts has determined that each CHF/DCM heart has an optimal short AV delay that generates the highest cardiac output and provides the most physiologic hemodynamics as measured using echocardiography. See, "Effect of pacing chamber and atrioventricular delay on acute systolic function of paced patients with congestive heart failure" by Auricchio A, Stellbrink C, et al., *CIRCULATION* 1999, June 15;99 (23):2993–3001.

Short AV delays in the range of 60 ms–140 ms are typically recommended for bi-ventricular pacing to ensure ventricular capture and appropriate left ventricular filling. The relatively short AV delay is most optimally determined by testing the cardiac hemodynamic performance at differing AV delays.

The pacing regimens provided by these three and four chamber pacing systems are intended to achieve a shortening of the abnormally wide, intrinsically exhibited QRS complex, which is an attribute of most hearts exhibiting CHF with bundle branch block as described above. However, certain hearts exhibiting CHF do not exhibit abnormally wide QRS complexes, and cardiac output is not necessarily improved when bi-ventricular pacing is applied as described above. In fact, the bi-ventricular pacing can unduly widen the resulting evoked QRS complexes.

Moreover, the relatively short AV delays can cause an evoked contraction of the ventricles before the ventricles fill with blood from the atria.

SUMMARY OF THE INVENTION

The inventor has discovered that in certain hearts exhibiting CHF, cardiac output is enhanced by timing the delivery of an LV-PACE pulse such that evoked depolarization of the LV is effected in fusion with the intrinsic depolarization of the RV. The fusion depolarization enhances cardiac output in such hearts where the RV depolarizes first due to intact A-V conduction of a preceding intrinsic or evoked atrial depolarization wave front, but the A-V conducted depolarization of the LV is unduly delayed. The fusion depolarization of the LV is attained by timing the delivery of the LV-PACE pulse to follow, in time, the intrinsic depolarization of the RV but to precede, in time, the intrinsic depolarization of the LV. Advantageously, an RV-PACE pulse is not delivered due to the inhibition of the RV-PACE upon the RV-EVENT, allowing natural propagation of the wave front and depolarization of the septum, while an LV-PACE pulse is prematurely delivered in fusion with the RV depolarization.

The present invention is preferably implemented into a DDD/DDDR or VDD/VDDR pacing system that is capable of pacing and/or sensing in at least one atrial heart chamber and pacing and sensing in both the RV and LV. In a preferred operating mode, an A-RVP delay between an atrial pace (A-PACE) or sense event (A-EVENT), preferably an A-EVENT, and the delivery of an RV-PACE is established to ensure that it is longer than a measured intrinsic A-RVs conduction time. A non-refractory RV-EVENT then usually occurs and terminates the A-RVp before the RV-PACE can be delivered. An A-LVp delay between the A-PACE or A-EVENT and the delivery of an LV-PACE is established to ensure that it is shorter by a Δ value than a measured intrinsic A-LVs conduction time so that the LV-PACE pulse is delivered while the RV is spontaneously depolarizing. Preferably, the A-LVp delay is constrained to always be longer than the intrinsic A-RVs delay. This form of fusion pacing advantageously provides the longest filling time of blood from the left atrium into the left ventricle and then provides coordinated pumping of the blood from the right and left ventricles so that cardiac function is optimized.

The A-LVp delay is preferably periodically derived as a function of a measurement of the intrinsic A-LVs delay that is decremented by the Δ value. The intrinsic A-RVs delay is also measured and compared to the derived A-LVp delay. If the derived A-LVp delay becomes substantially equal to or shorter than the intrinsic A-RVs delay, then the A-RVp delay is decremented to be shorter than the A-LVp delay. Bi-ventricular pacing of the RV and LV is then established closely timed to the intrinsic RV and LV depolarizations. This back-up bi-ventricular pacing advantageously still maximizes the A-RVp and A-LVp delays and provides optimal cardiac function.

The above-described algorithm specifically applies to the case where the left ventricular activation follows the depolarization of the right ventricle after an inappropriate delay. It will be understood that the above-described algorithm can be employed in situations where this relation is reversed (e.g., RBBB).

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail in FIGS. 2 and 3 in the context of an AV sequential, bi-ventricular, pacing system operating in demand, atrial tracking, and triggered pacing modes in accordance with FIGS. 4 through 7 for restoring synchrony in depolarizations and contraction of the LV and RV in synchronization with atrial paced and/or atrial sensed events. This embodiment of the invention is programmable to operate as a three chamber pacing system having an AV synchronous operating mode for restoring upper and lower heart chamber synchronization and right and left atrial and/or ventricular chamber depolarization synchrony. The system can comprise the capabilities of one of the DDD/DDDR and VDD/DDR bi-ventricular pacing systems but preferably operates in the VDD operating mode wherein intrinsic atrial events govern the timing of the A-LVp and A-RVp delays. Of course, the present invention may also be practiced in a simpler, three-chamber VDD pacing system eliminating certain of the features of the preferred embodiment described herein.

It should be appreciated that the present invention may be utilized particularly to treat patients suffering various forms of heart failure, ventricular dysfunction or bradycardia. The pacing system of the present invention can also be incorporated into an anti-tachyarrhythmia system including specific high rate pacing and cardioversion shock therapies for providing staged therapies to treat a diagnosed tachyarrhythmia.

Figure 1:
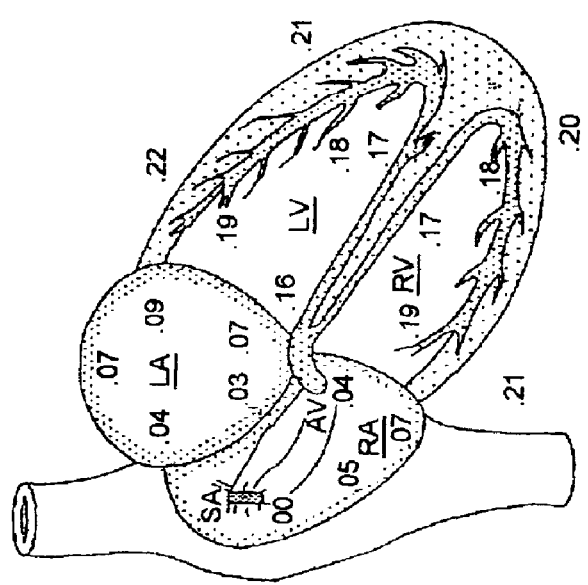
FIG. 1 is an illustration of transmission of the cardiac depolarization waves through the heart in a normal electrical activation sequence.

In accordance with an aspect of the present invention, a method and apparatus is provided to restore the depolarization sequence of FIG. 1 and the synchrony between the RV, septum, and LV that contributes to adequate cardiac output related to the optimal timed depolarizations of the RV and LV. This restoration is effected through providing optimally timed cardiac pace pulses to the LV and, as necessary, to the RV accounting for the particular implantation sites of the pace/sense electrodes in relation to each heart chambers.

Figure 2:
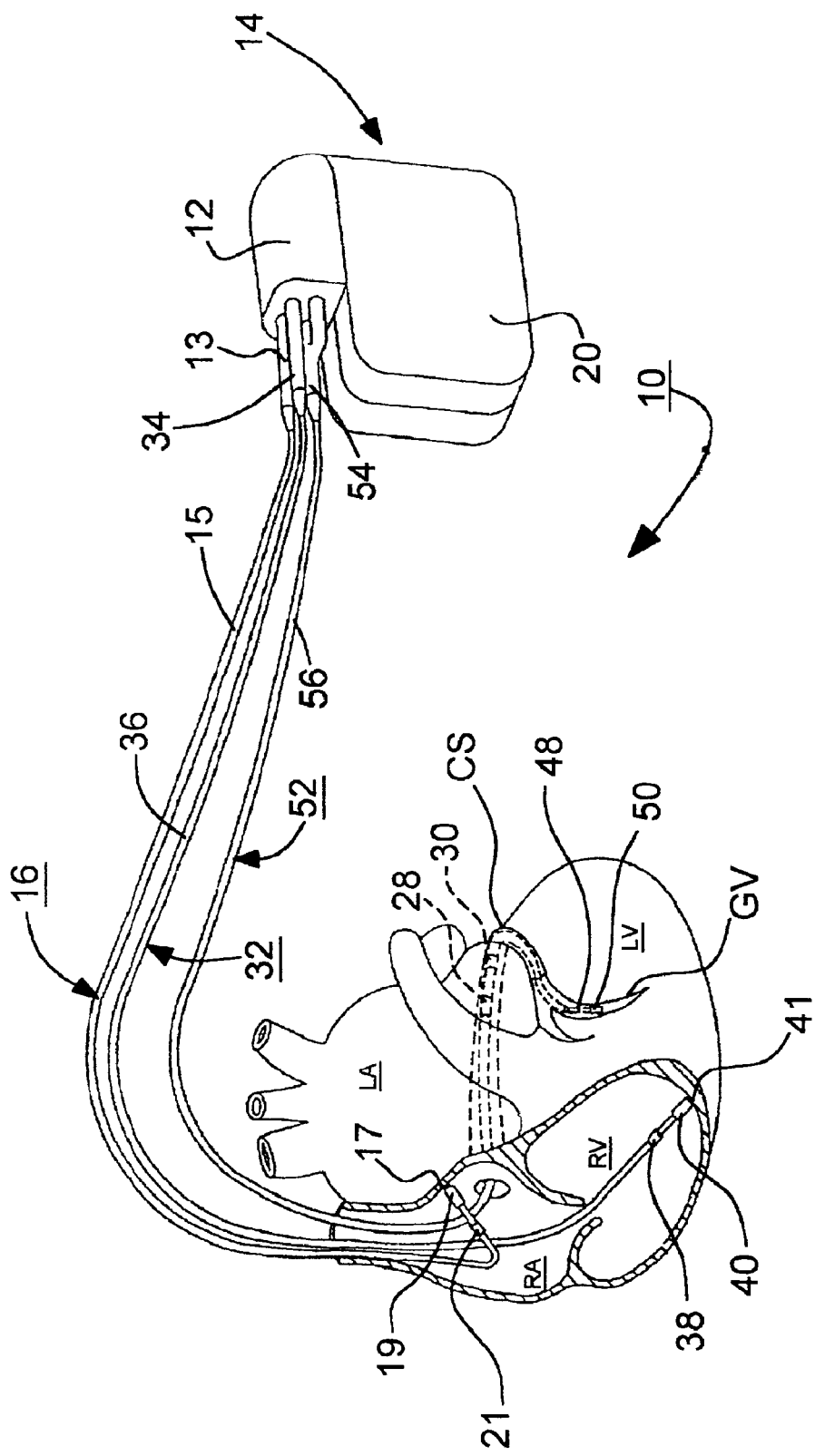
FIG. 2 is a schematic diagram depicting a three channel, atrial and bi-ventricular, pacing system in which the present invention is preferably implemented.

FIG. 2 is a schematic representation of an implanted, three chamber cardiac pacemaker comprising a pacemaker IPG 14 and associated leads 16, 32 and 52 in which the present invention may be practiced. The pacemaker IPG 14 is implanted subcutaneously in a patient's body between the skin and the ribs. The three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals, e.g. a far field R-wave (FFRS). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a bipolar, endocardial coronary sinus (CS) lead 52 is passed through a vein and the RA chamber of the heart 10, into the coronary sinus and then inferiorly in a branching vessel to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein.

In a four chamber or channel embodiment, LV CS lead 52 could bear proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV.

In this case, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 3:
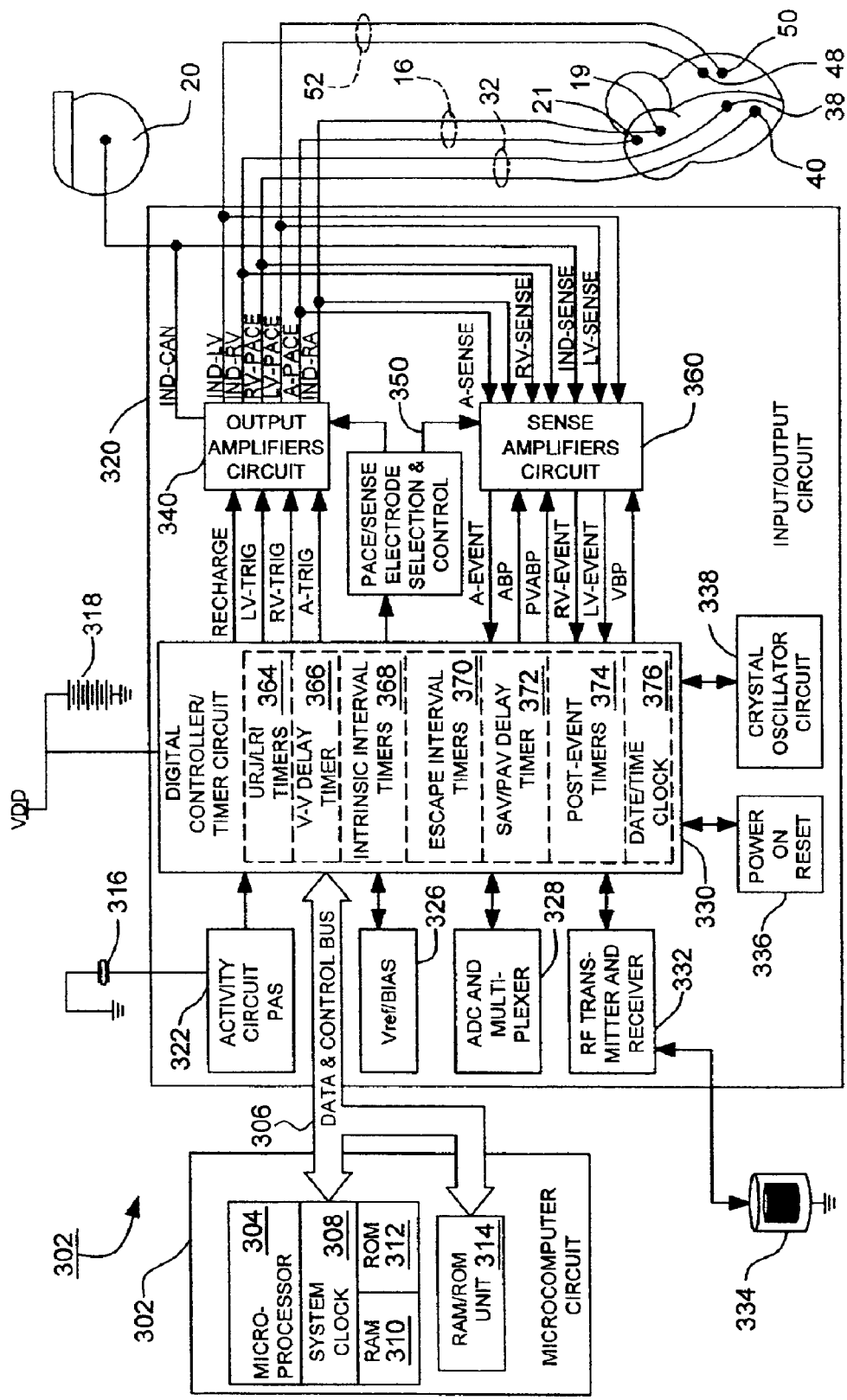
FIG. 3 is a simplified block diagram of one embodiment of IPG circuitry and associated leads employed in the system of FIG. 2 for providing three pacing channels that selectively functions in atrial synchronous, left ventricular or bi-ventricular pacing modes.

In this regard, FIG. 3 depicts bipolar RA lead 16, bipolar RV lead 32, and bipolar LV CS lead 52 without the LA CS pace/sense electrodes 28 and 30 coupled with an IPG circuit 300 having programmable modes and parameters of a bi-ventricular DDDR type known in the pacing art. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 322, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 332 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, LV-TRIG signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A or V-V escape interval. In addition, the microprocessor 304 may also serve to define variable AV delays and the bi-ventricular V-V pace delays from the activity sensor data.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include URI/LRI timers 364, V-V delay timer 366, intrinsic interval timers 368 for timing elapsed V-EVENT to V-EVENT intervals or V-EVENT to A-EVENT intervals or the V-V conduction interval, escape interval timers 370 for timing A-A, V-A, and/or V-V pacing escape intervals, an AV delay interval timer 372 for timing the A-LVp delay and A-RVp delay from a preceding A-EVENT or A-TRIG, a post-ventricular timer 374 for timing post-ventricular time periods, and a date/time clock 376.

Figure 7:
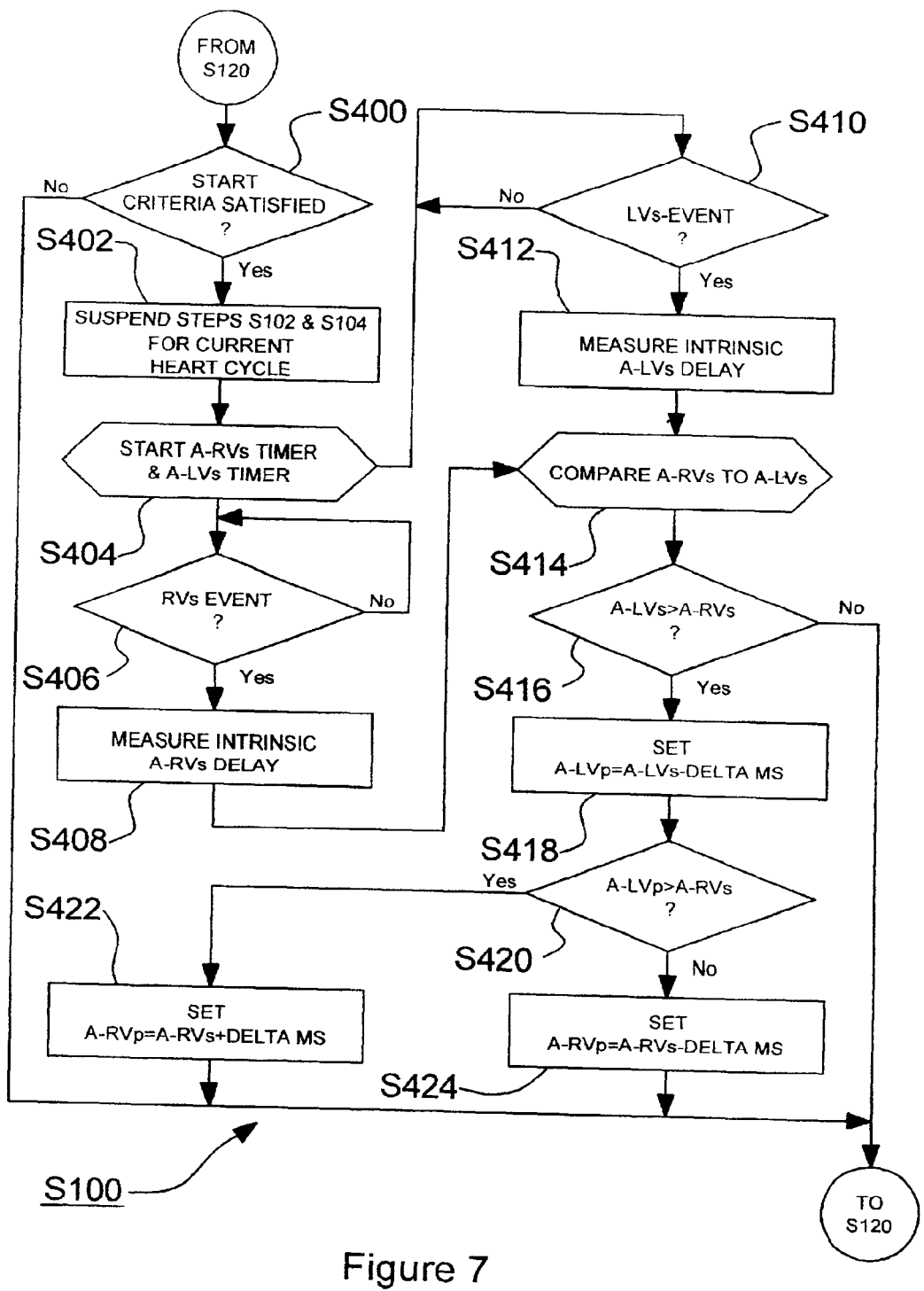
FIG. 7 is a flow chart illustrating the steps in step S100 of FIG. 4 of periodically deriving the A-RVp delay and the A-LVp delay as a function of the measured A-LVs delay.

In the present invention, the AV delay interval timer 372 is loaded with an appropriate A-RVP delay and an A-LVp delay as determined in FIG. 7 to time-out starting from a preceding A-PACE or A-EVENT. It should be noted that the V-V delay timer 366 could be employed to time out an equivalent V-V delay that represents the difference between the A-RVp delay and the A-LVp delay as determined in FIG. 7. In that case, the difference between the A-RVp delay and the longer A-LVp delay would be determined following the completion of the steps of FIG. 7. The interval timer 372 would time out the A-RVP delay, but typically not generate the RV-TRIG because of an RV-EVENT interrupting the timing, and then the V-V delay timer 366 would time out the difference and generate the LV-TRIG signal.

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting any AV delay, and an atrial blanking period (ABP) during which atrial sensing is disabled.

It should be noted that the starting of the post-atrial time periods and the AV delays can be commenced substantially simultaneously with the start or end of the A-EVENT or the A-TRIG or, in the latter case, upon the start of end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the start of end of the V-PACE which may follow the V-TRIG.

The microprocessor 304 also optionally calculates AV delays, post-ventricular time periods, and post-atrial time periods that vary with the sensor based escape interval established in response to the RCP(s) and/or with the intrinsic atrial rate.

The output amplifiers circuit 340 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates the RV-TRIG signal at the time-out of the A-RVp delay and the LV-TRIG at the time-out of the A-LVp delay provided by AV delay interval timer 372 (or the V-V delay timer 366). Similarly, digital controller/timer circuit 330 generates an RA-TRIG signal that triggers output of an RA-PACE pulse (or an LA-TRIG signal that triggers output of an LA-PACE pulse if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

To simplify the description of FIGS. 4 through 7, it will be assumed that the following references to an "A-EVENT" and "A-PACE" will be the RA-EVENT and RA-PACE, respectively, if there is no LA pacing or sensing provided or programmed on, or will be a programmed one of the RA-EVENT or LA-EVENT and RA-PACE or LA-PACE, respectively.

Figure 4:
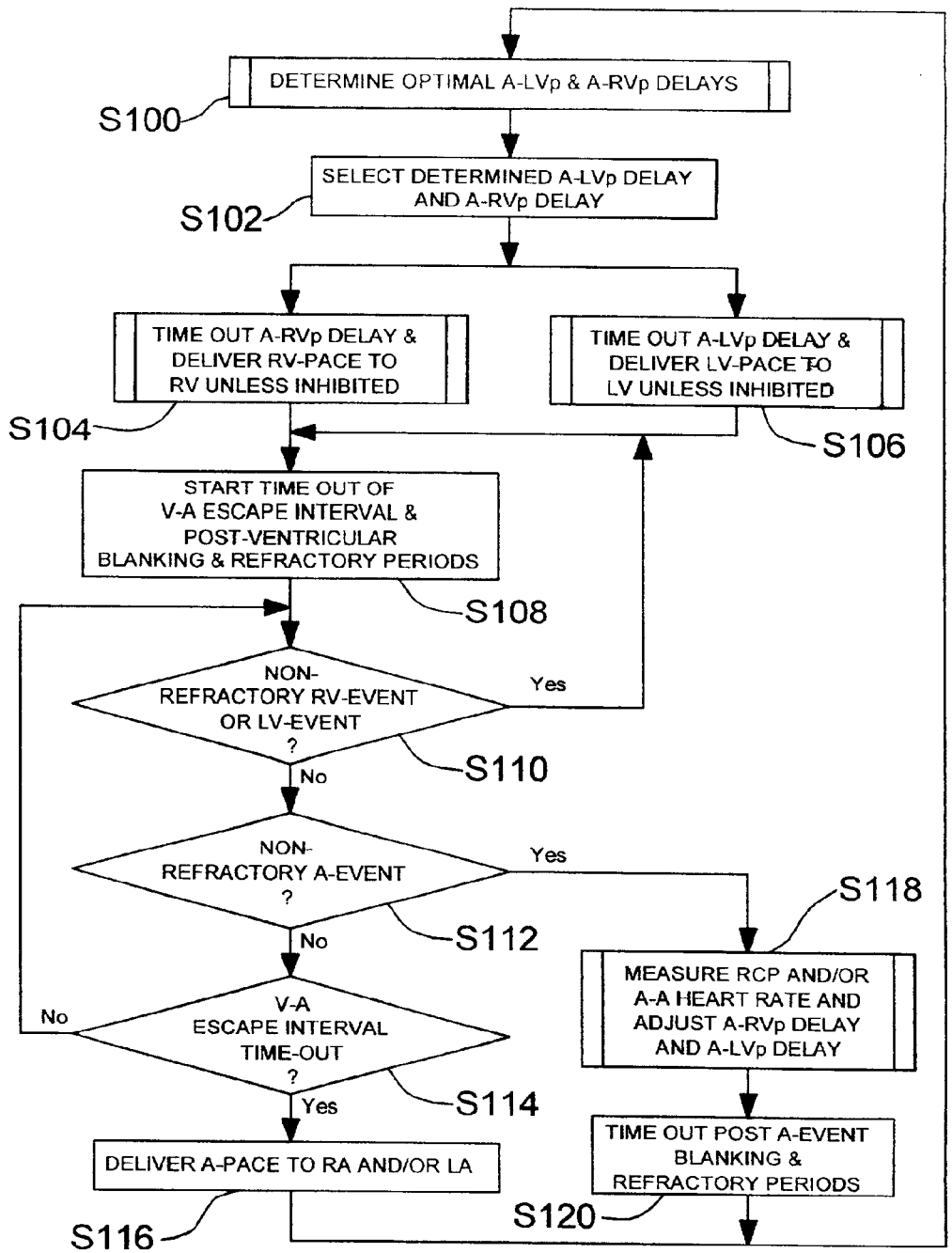
FIG. 4 is a comprehensive flow-chart illustrating a preferred VDD or DDD operating mode of the IPG circuitry of FIG. 3 providing bi-ventricular pacing in accordance with one embodiment of the invention.

The possible operating modes of IPG circuit 300 are depicted in the flow chart of FIGS. 4–7 and described as follows. The particular operating mode of the present invention is a programmed or hard-wired sub-set of the possible operating modes as also described below. FIG. 4 illustrates the overall operations of the IPG circuit 300 during each pacing cycle and includes a further step S100 that is periodically entered into to derive the A-RVp and A-LVp delays (illustrated in FIG. 7) that are timed out in steps S104 (illustrated in FIG. 5) and S106 (illustrated in FIG. 6).

For convenience, the algorithm of FIGS. 4–7 is described as follows in the context of determining the A-RVp and A-LVp delays to optimally pace the left ventricle in fusion with an earlier, in time, depolarization of the right ventricle, which preferably depolarizes spontaneously after an intrinsic A-RVs delay as one example of the operations of the algorithm. As noted below, the algorithm can be employed to determine the A-RVp and A-LVp delays to optimally pace the right ventricle in fusion with an earlier, in time, depolarization of the left ventricle, which preferably depolarizes spontaneously after an intrinsic A-LVs delay.

When steps S104 and S106 are concluded it is expected that at least the LV-PACE will have been delivered, and time-out of the escape interval, e.g., a V-A escape interval, and the post-ventricular blanking and refractory periods is started in step S108. The RV and LV sense amplifiers and the atrial sense amplifier are enabled after the blanking periods to detect R-WAVES and P-waves and declare an RV-EVENT and an LV-EVENT in step S110 and an A-EVENT in step S112 during the time-out of the escape interval. The time-out of the escape interval is terminated and restarted upon declaration of any of any non-refractory RV-EVENT and LV-EVENT in step S110. The time-out of the escape interval is terminated or upon declaration of an A-EVENT in step S112 causing the A-RVp delay to be restarted in step S104 and the A-LVp delay to be restarted in step S106, unless the step of determining the optimal A-RVp delay and the A-LVp delay to be determined in step S100 as described below in reference to FIG. 7. The escape interval can be fixed as a programmed value in the VDD and DDD pacing mode or vary between programmed LPL and URL as a function of the RCP algorithm in VDDR and DDDR pacing modes An A-PACE, comprising one (or both) of the RA-PACE and LA-PACE pulses, is delivered in step S116 if the V-A escape interval does time out as determined in step S114. It would be expected in practice that the V-A escape interval would be programmed to be greater than the intrinsic heart rate in patients whose atrial function is intact and provides normal sinus rhythm. Or, the pacing system can be provided as a VDD/DDR pacing system, eliminating sensing of P-waves. So, steps S114 and S116 would not be followed in such cases.

The intrinsic A-EVENT, comprising one of the RA-EVENT and the LA-EVENT, would therefore be more likely declared in step S112. Step S118 is optionally bypassed or practiced to adjust one or both of the A-RVp delay and the A-LVp delay as a function of the RCP algorithm or the measured, current intrinsic A-A interval. Then, the post-atrial blanking and refractory time periods are timed out in step S120, and the A-RVp delay is restarted in step S104 (FIG. 5) and the A-LVp delay is restarted in step S106 (FIG. 6), unless step S100 determining the optimal A-RVp delay and the A-LVp delay is entered as described below in reference to FIG. 7. It would be expected that step S100 would be practiced periodically at a programmed time of day, e.g., at night when the patient would be expected to be resting and heart rate and activity criteria are met, when an LV-EVENT is declared during time-out of the A-LVp delay, or when the RCP suggests a patient activity level exceeding a certain threshold.

Figure 5:
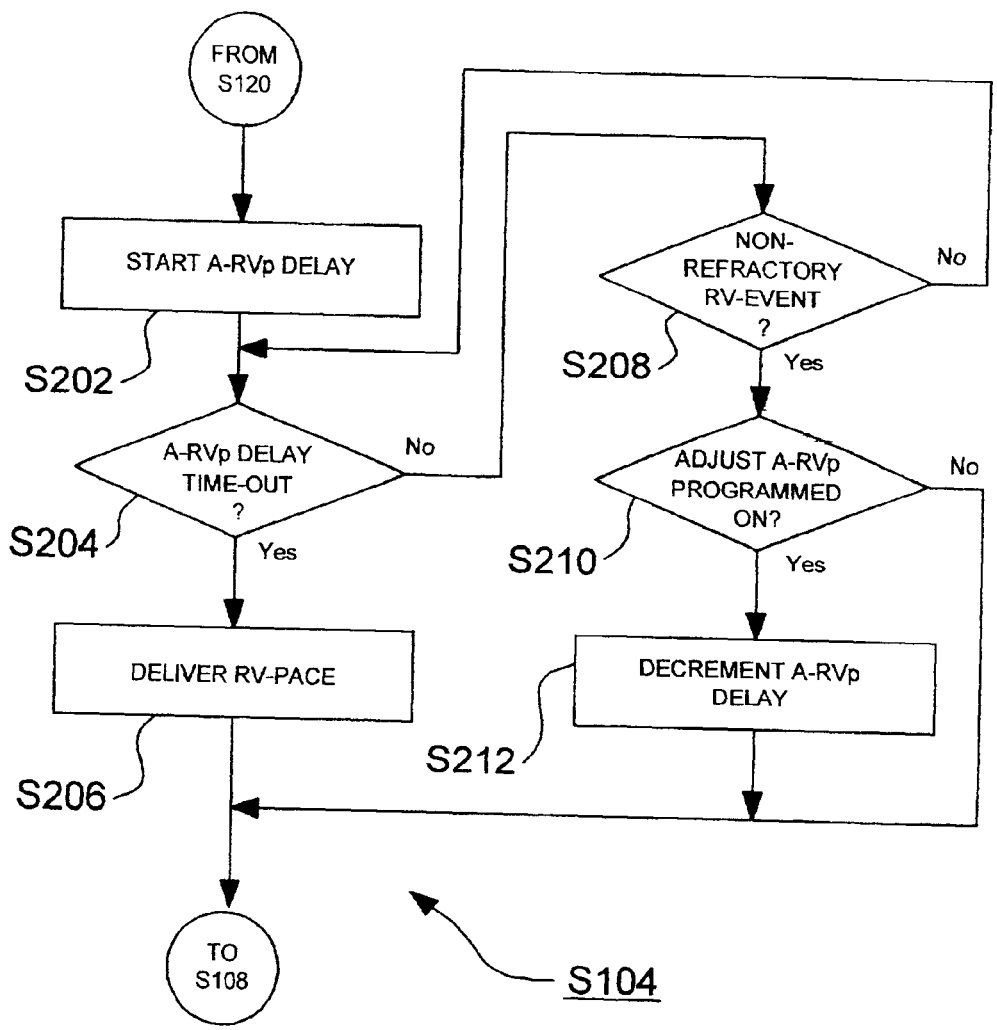
FIG. 5 is a flow chart illustrating the steps in step S104 of FIG. 4 of delivering an RV-PACE pulse following time-out of an A-RVp delay unless an RV-EVENT terminates the A-RVp delay.

In FIG. 5, the A-RVp delay is started in step S202 and timed out in step S204. As noted above, the A-RVp delay would normally be set to exceed the intrinsic A-RVs conduction time of the depolarization wave front from the atrium to the location of the RV sense electrodes, and so the delivery of the RV-PACE in step S206 would ordinarily be inhibited. However, there are conditions described further below where the A-RVp delay is shortened in step S100 such that the RV-PACE would be more likely to be delivered. When a non-refractory RV-EVENT is declared in step S208, then the algorithm advances to step S108 unless an optional feature is programmed ON as determined in step S210 to decrement the A-RVp delay in step S212.

Figure 6:
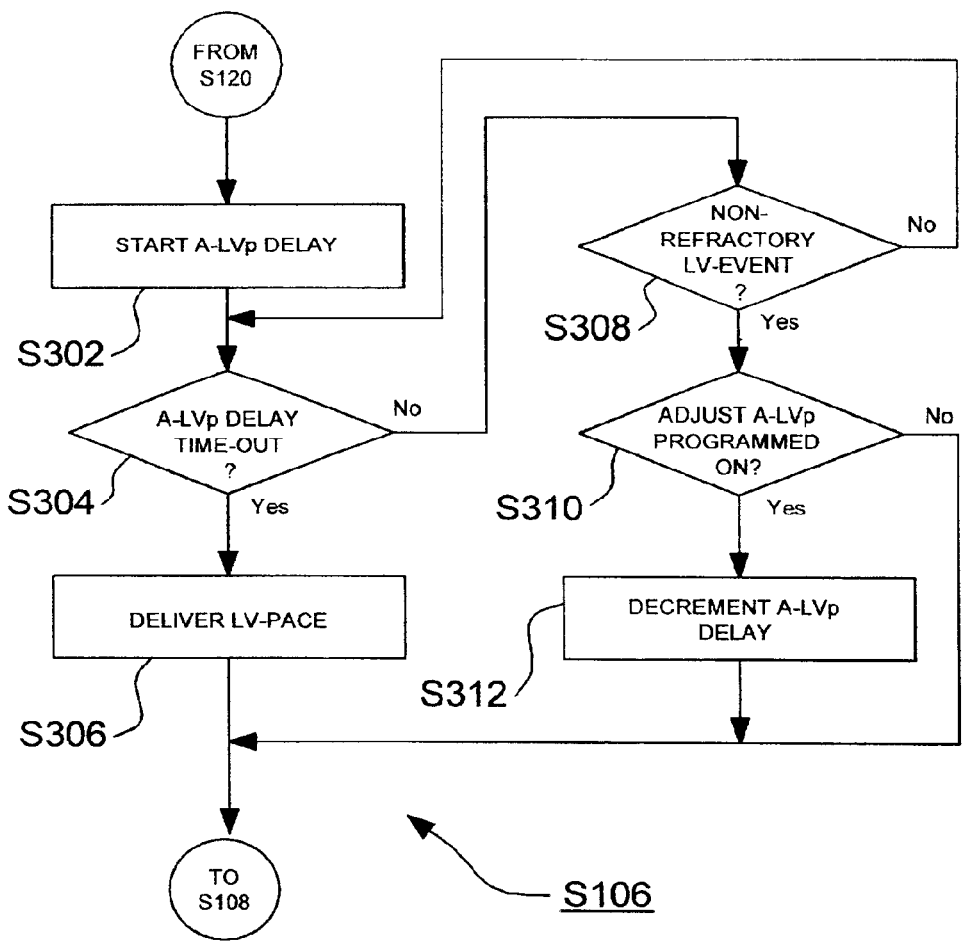
FIG. 6 is a flow chart illustrating the steps in step S106 of FIG. 4 of delivering an LV-PACE pulse following time-out of an A-LVp delay unless an LV-EVENT terminates the A-LVp delay.

In FIG. 6, the A-LVp delay is started in step S302 and timed out in step S304. As noted above, the A-LVp delay would normally be set to be shorter than the intrinsic A-LVs conduction time of the depolarization wave front from the atrium to the location of the LV sense electrodes, and so the LV-PACE would typically be delivered in step S306. However, there are conditions described further below where the LV-EVENT might be declared and the A-LVp delay shortened in step S100 such that the LV-PACE would be more likely to be delivered. In this case, when a non-refractory LV-EVENT is declared in step S308, the algorithm advances to step S108 unless an optional feature is programmed ON as determined in step S310 to decrement the A-LVp delay in step S312.

The adjustments to the A-RVp delay in step S212 and the A-LVp delay in step S312 can be programmed ON if it is found that the adjustments maintain the maximal filling time and maintain the improved coordination of RV and LV contraction effected by the delivery of the RV-PACE and/or LV-PACE in accordance with the algorithm of FIGS. 4–7. It is envisaged that other events could trigger adjustment of the A-RVp delay and/or the A-LVp delay as a function of changes in the intrinsic escape interval evidenced by a measured A-A interval, changes in the patient's physiologic requirements as evidenced by the RCP, or blood pressure or other sensor signals that are suggestive of a conduction delay or activation adjustment.

The adjustment step S100, illustrated in greater detail in FIG. 7, is commenced when the start criteria are met in step S400. Steps S102 and S104 are suspended until the declaration of the next A-EVENT or a number of A-EVENTS are counted. An A-RVs timer and an A-LVs timer are started in step S404 to enable determination of the intrinsic A-RVs delay in steps S406 and S408 and the intrinsic A-LVs delay in steps S410 and S412. Then, the intrinsic A-RVs delay and the intrinsic A-LVs delay are compared in step S414 to ensure that the intrinsic A-RVs delay exceeds the intrinsic A-LVs delay in step S416. Step S416 would be expected to be satisfied when the left ventricular activation is delayed in comparison to the right ventricular activation (e.g., LBBB).

In step S418, the A-LVp delay is adjusted to reflect the current measured intrinsic A-LVs delay by the formula A-LVp=A-LVs−Δ ms, where Δ ms is a programmed value, e.g., 10 ms, or is a an adaptive value, e.g., a percentage, e.g., 10%, of the measured intrinsic A-LVs conduction delay or the A-LVs/measured intrinsic A-A cycle length.

The adjusted A-LVP delay is then compared to the A-RVs in step S420 to ensure that the adjusted A-LVp delay is greater than the intrinsic A-RVs delay. If that condition is satisfied, then the A-RVp delay can be set to be longer than the measured intrinsic A-RVs delay in step S422 by the formula A-RVp=A-RVs+Δ ms, where Δ ms is a programmed value, e.g., 10 ms, or is a an adaptive value, e.g., a percentage, e.g., 10%, of the measured intrinsic A-LVs conduction delay or the A-LVs/measured intrinsic A-A cycle length or is programmed to zero.

If step S422 is followed, then the RV will not be paced, and the LV will be paced in fusion with the intrinsic depolarization of the RV.

If the condition of step S420 is not satisfied, then it is necessary to revert to bi-ventricular pacing wherein an RV-PACE is first delivered and an LV-PACE is then delivered. In step S424, the A-RVp delay is adjusted to reflect the current measured intrinsic A-RVs delay by the formula A-RVp=A-RVs−Δ ms, where Δ ms is a programmed value, e.g., 10 ms, or is a an adaptive value, e.g., a percentage, e.g., 10%, of the measured intrinsic A-LVs conduction delay or the A-LVs/measured intrinsic A-A cycle length.

The updated determined A-RVp and A-LVp delays are then stored in RAM memory to be employed in the pacing operating mode of FIG. 4 until the start criteria of step S400 are again satisfied and the A-RVp and A-LVp delays are again determined.

The above-described algorithm specifically applies to the case where the left ventricular activation follows the depolarization of the right ventricle after an inappropriate delay, e.g. a heart exhibiting LBBB. It will be understood that the above-described algorithm could be employed in situations where this relation is reversed, e.g., a heart exhibiting RBBB. In that case, the steps of the above-described algorithm could be followed substituting the operations pertaining to the right ventricle for those pertaining to the left ventricle.

Therefore, it will be understood that the present invention comprises a cardiac pacing system for and method of delivering ventricular pacing pulses to at least one of the right and left ventricles of the heart (which can be designated V1) wherein the delivery of the ventricular pacing pulse follows a preceding atrial event and follows, in time, the depolarization of the other of the right and left ventricles (which can be designated V2). In the above-described example, V1 comprises the left ventricle LV, and V2 comprises the right ventricle RV. However, V1 can comprise the right ventricle V2, and V1 can comprise the left ventricle. Therefore, the steps of the algorithm of FIGS. 4–7 can also be expressed substituting V1 for LV and V2 for RV. A ventricular atrio-ventricular delay (A-V1$p$) from an atrial event (A) to time the delivery of a ventricular pacing pulse (V1$p$) to ventricle V1 is thus established by: (1) sensing ventricular depolarizations of ventricle V1 as a ventricular sense (V1$s$) event; (2) measuring the intrinsic atrial-ventricular delay between an atrial event and the V1$s$ event as an intrinsic A-V1$s$ delay; (3) sensing ventricular depolarizations of the ventricle V2 as a ventricular sense (V2$s$) event; (4) measuring the intrinsic atrial-ventricular delay between an atrial event and the V2$s$ event as an intrinsic A-V2$s$ delay; and (5) determining an atrio-ventricular A-V1$p$ delay that is shorter than the intrinsic A-V1$s$ delay and longer than the intrinsic A-V2s delay. The A-V1p delay is timed from each atrial event, and the ventricular pacing pulse V1p is delivered to the ventricle V1 at the timeout of the A-V1p delay to effect fusion pacing of the ventricle V1 with intrinsic depolarization of the ventricle V2.

CONCLUSION

All patents and publications referenced herein are hereby incorporated by reference in their entireties.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of an AV synchronous, three or four chamber pacemaker that are not disclosed and are not necessary to the practice of the present invention. In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. In a multi-site, cardiac pacing system for delivering ventricular pacing pulses, a method of timing the delivery of left ventricular pacing pulses from a preceding atrial event and following, in time, the depolarization of the right ventricle comprising:

establishing a left ventricular atrial-ventricular delay (A-LVp) from an atrial event (A) to time the delivery of a left ventricular pacing pulse (LVp) by:
sensing ventricular depolarizations of the left ventricle as a left ventricular sense (LVs) event;
measuring the intrinsic atrial-left ventricular delay between an atrial event and the LVs event as an intrinsic A-LVs delay;
sensing ventricular depolarizations of the right ventricle as a right ventricular sense (RVs) event;
measuring the intrinsic atrial-right ventricular delay between an atrial event and the RVs event as an intrinsic A-RVs delay; and
determining an A-LVp delay that is shorter than the intrinsic A-LVs delay and longer than the intrinsic A-RVs delay;

starting an A-LVp delay timer from an atrial event (A); and delivering a left ventricular pacing pulse to the left ventricle when the A-LVp delay timer reaches the determined A-LVp delay to effect fusion pacing of the left ventricle with intrinsic depolarization of the right ventricle.

2. The method of claim 1, wherein the determining step further comprises setting the determined A-LVp delay to be shorter than the intrinsic A-LVs delay by a programmable factor.

3. The method of claim 2, further comprising:
comparing the determined A-LVp delay with the intrinsic A-RVs delay;
if the determined A-LVp delay is shorter than the intrinsic A-RVs delay, then determining a right ventricular A-RVp delay that is shorter than the intrinsic A-RVs delay and the determined A-LVp; and timing out the A-RVp delay from the atrial event and delivering a right ventricular pacing pulse to the right ventricle at the time-out of the A-RVp delay to effect bi-ventricular pacing of the right ventricle and the left ventricle.

4. The method of claim 2, further comprising:
comparing the determined A-LVp delay with the intrinsic A-RVs delay;
if the determined A-LVp delay is longer than the intrinsic A-RVs delay, then determining a right ventricular A-RVp delay that is longer than the intrinsic A-RVs delay.

5. The method of claim 4, further comprising:
comparing the determined A-LVp delay with the intrinsic A-RVs delay;
if the determined A-LVp delay is shorter than the intrinsic A-RVs delay, then determining a right ventricular A-RVp delay that is shorter than the intrinsic A-RVs delay and the determined A-LVp; and timing out the A-RVp delay from the atrial event and delivering a right ventricular pacing pulse to the right ventricle at the time-out of the A-RVp delay to effect bi-ventricular pacing of the right ventricle and the left ventricle.

6. The method of claim 1, further comprising:
comparing the determined A-LVp delay with the intrinsic A-RVs delay;
if the determined A-LVp delay is shorter than the intrinsic A-RVs delay, then determining a right ventricular A-RVp delay that is shorter than the intrinsic A-RVs delay and the determined A-LVp; and timing cut the A-RVp delay from the atrial event and delivering a right ventricular pacing pulse to the right ventricle at the time-out of the A-RVp delay to effect bi-ventricular pacing of the right ventricle and the left ventricle.

7. The method of claim 1, further comprising:
monitoring a rate control parameter indicative of the patient's physiological demand for cardiac output; and
adjusting the determined A-LVp delay to reflect the monitored rate control parameter.

8. The method of claim 7, wherein the adjusting step further comprises:
decreasing the A-LVp delay when the monitored rate control parameter signifies an increased demand for cardiac output; and
increasing the A-LVp delay when the monitored rate control parameter signifies a decreased demand for cardiac output.

9. The method of claim 1, further comprising:
monitoring the intrinsic atrial rate of the patient's heart; and
adjusting the determined A-LVp to reflect the monitored atrial rate.

10. The method of claim 9, wherein the adjusting step further comprises:
decreasing the A-LVp delay when the monitored intrinsic atrial rate shortens; and increasing the A-LVp delay when the monitored intrinsic atrial rate lengthens.

11. The method of claim 1, further comprising:
sensing any intrinsic LVs event during time-out of the A-LVp delay; and
decreasing the A-LVp delay in response to a sensed intrinsic LVs event.

12. The method of claim 1, further comprising:
sensing any intrinsic RVs event during time-out of the A-RVp delay; and
decreasing the A-RVp delay in response to a sensed intrinsic RVs event.

13. A multi-site, cardiac pacing system for delivering ventricular pacing pulses to a left ventricular site of the heart synchronously timed from a preceding atrial event and following, in time, the depolarization of the right ventricle comprising:
left ventricular sense means for sensing ventricular depolarizations of the left ventricle as a left ventricular sense (LVs) event;
means for measuring the intrinsic atrial-left ventricular delay between an atrial event and the LVs event as an intrinsic A-LVs delay;
right ventricular sense means for sensing ventricular depolarizations of the right ventricle as a right ventricular sense (RVs) event;
means for measuring the intrinsic atrial-right ventricular delay between an atrial event and the RVs event as an intrinsic A-RVs delay;
means for determining a left ventricular A-LVp delay that is shorter than the intrinsic A-LVs delay and longer than the intrinsic A-RVs delay;
means for timing out the A-LVp delay from tile atrial event; and
means for delivering a left ventricular pacing pulse to the left ventricle at the time-out of the A-LVp delay to effect fusion pacing of the left ventricle with intrinsic depolarization of the right ventricle.

14. The system of claim 13, wherein the determining means comprises
means for setting the A-LVp delay to be shorter than the intrinsic A-LVs delay by a programmable factor.

15. The system of claim 14, wherein the determining means further comprises:
means for comparing the determined A-LVp delay with the intrinsic A-RVs delay; and
means for determining a right ventricular A-RVp delay that is shorter than the intrinsic A-RVs delay and the determined A-LVp in the event that the determined A-LVp delay is shorter than the intrinsic A-RVs delay; and further comprising:
means for timing out the determined right ventricular A-RVp delay from the atrial event and delivering a right ventricular pacing pulse to the right ventricle at the time-out of the determined right ventricular A-RVp delay to effect bi-ventricular pacing of the right ventricle and the left ventricle.

16. The system of claim 13, further comprising:
means for monitoring a rate control parameter indicative of the patient's physiological demand for cardiac output; and
means for adjusting the determined A-LVp delay to reflect the monitored rate control parameter.

17. The system of claim 16, wherein the adjusting means further comprises:
means for decreasing the A-LVp delay when the monitored rate control parameter signifies an increased demand for cardiac output; and
increasing the A-LVp delay when the monitored rate control parameter signifies an decreased demand for cardiac output.

18. The system of claim 13, further comprising:
means for monitoring the intrinsic atrial rate of the patient's heart; and
means for adjusting the determined A-LVp to reflect the monitored atrial rate.

19. The system of claim 18, wherein the adjusting means further comprises:
means for decreasing the A-LVp delay when the monitored intrinsic atrial rate shortens; and
means for increasing the A-LVp delay when the monitored intrinsic atrial rate lengthens.

20. The system of claim 13, further comprising:
means for sensing any intrinsic LW event during time-out of the A-LVp delay; and
means for decreasing the A-LVp delay in response to a sensed intrinsic LVs event.

21. The system of claim 13, further comprising:
means for sensing any intrinsic RVs event during time-out of the A-RVp delay; and
means for decreasing the A-RVp delay in response to a sensed intrinsic RVs event.

22. In a multi-site, cardiac pacing system for delivering ventricular pacing pulses to at least one of the right and left ventricles of the heart (V1), a method of timing the delivery of the ventricular pacing pulse from a preceding atrial event and following, in time, the depolarization of the other of the right and left ventricles (V2) comprising:
establishing an atria-ventricular delay (A-V1$p$) from an atrial event (A) to time the delivery of a ventricular pacing pulse (V1$p$) to ventricle V1 by:
sensing ventricular depolarizations of ventricle V1 as a ventricular sense (V1$s$) event;
measuring the intrinsic atrial-ventricular delay between an atrial event and the V1$s$ event as an intrinsic A-V1$s$ delay;
sensing ventricular depolarizations of the ventricle V2 as a ventricular sense (V2$s$) event;
measuring the intrinsic atrial-ventricular delay between an atrial event and the V2$s$ event as an intrinsic A-V2$s$ delay; and
determining an atrio-ventricular A-V1$p$ delay that is shorter than the intrinsic A-V1$s$ delay and longer than the intrinsic A-V2$s$ delay;
timing out the A-V1$p$ delay from each atrial event; and
delivering ventricular pacing pulse V1$p$ to the ventricle V1 at the time-cut of the A-V1$p$ delay to effect fusion pacing of the ventricle V1 with intrinsic depolarization of the ventricle V2.

23. The method of claim 22, wherein the ventricle V1 comprises the right ventricle and the ventricle V2 comprises the left ventricle.

24. The method of claim 22, wherein the ventricle V1 comprises the left ventricle and the ventricle V2 comprises the right ventricle.

25. A cardiac pacing system for delivering ventricular pacing pulses to at least one of the right and left ventricles of the heart (V1) timed from a preceding atrial event and following, in time, the depolarization of the other of the right and left ventricles (V2) comprising:
means for establishing an atrio-ventricular delay (A-V1$p$) from an atrial event (A) to time the delivery of a ventricular pacing pulse (V1$p$) to ventricle V1 by:
sensing ventricular depolarizations of ventricle V1 as a ventricular sense (V1$s$) event;

measuring the intrinsic atrial-ventricular delay between an atrial event and the V1s event as an intrinsic A-V1s delay;

sensing ventricular depolarizations of the ventricle V2 as a ventricular sense (V2s) event:

measuring the intrinsic atrial-ventricular delay between an atrial event and the V2s event as an intrinsic A-V2s delay; and determining an atrio-ventricular A-V1p delay that is shorter than the intrinsic A-V1s delay and longer than the intrinsic A-V2s delay;

means for timing out the A-V1p delay from each atrial event; and means for delivering ventricular pacing pulse V1p to the ventricle V1 at the time-out of the A-V1p delay to effect fusion pacing of the ventricle V1 with intrinsic depolarization of the ventricle V2.

26. The system of claim 25, wherein the ventricle V1 comprises the right ventricle and the ventricle V2 comprises the left ventricle.

27. The system of claim 25, wherein the ventricle V1 comprises the left ventricle and the ventricle V2 comprises the right ventricle.

* * * * *

UNITED STATES PATENT AND TRADEMARK OFFICE
CERTIFICATE OF CORRECTION

PATENT NO. : 6,871,096 B2 Page 1 of 1
APPLICATION NO. : 10/000474
DATED : March 22, 2005
INVENTOR(S) : Michael R.S. Hill It is certified that error appears in the above-identified patent and that said Letters Patent is hereby corrected as shown below:

Col. 20, line 14, please delete "LW event" and insert --LVs event--

Signed and Sealed this

Nineteenth Day of December, 2006

JON W. DUDAS
*Director of the United States Patent and Trademark Office*